United States Patent [19]

Lathan et al.

[11] Patent Number: 5,137,697
[45] Date of Patent: Aug. 11, 1992

[54] OZONE GENERATOR

[75] Inventors: James R. Lathan; Michael J. Ferrante, both of Warwick, R.I.

[73] Assignee: Quantum Electronics Corporation, Warwick, R.I.

[21] Appl. No.: 704,822

[22] Filed: May 23, 1991

[51] Int. Cl.$^5$ .............................................. B01J 19/12
[52] U.S. Cl. ................................ 422/186.15; 204/176
[58] Field of Search ............. 422/186, 186.04, 186.07, 422/186.1, 186.21, 186.27, 186.15

[56] References Cited

U.S. PATENT DOCUMENTS

| | | |
|---|---|---|
| 829,790 | 8/1906 | Joseph . |
| 2,113,913 | 4/1938 | Cragun .......................... 422/186.07 |
| 2,952,606 | 9/1960 | Pascale et al. . |
| 3,457,160 | 7/1969 | Fortier . |
| 3,745,750 | 7/1973 | Arff ........................................ 55/102 |
| 3,844,741 | 10/1974 | Dimitrik ................................ 55/102 |
| 4,713,220 | 12/1987 | Huynh et al. .................. 422/186.16 |

Primary Examiner—Brooks H. Hunt
Assistant Examiner—Daniel J. Jenkins
Attorney, Agent, or Firm—Barlow & Barlow Ltd.

[57] ABSTRACT

An air purifying apparatus that has an ozone generator which generates plasma field in the ultraviolet region. It utilizes a pair of electrodes in the form of plates that are separated by an insulator. The plates are connected to a high-voltage transformer through diodes in such a way that only a negative and less positive charges appear on the plates. The generator is provided with a self-cleaning apparatus in which the circulating air fan that is provided for normally forcing air through the electrostatic plates may be turned off for a period of time and the ozone generated by the plates at that point in time will tend to combine with the contaminates and oxidize the same.

7 Claims, 1 Drawing Sheet

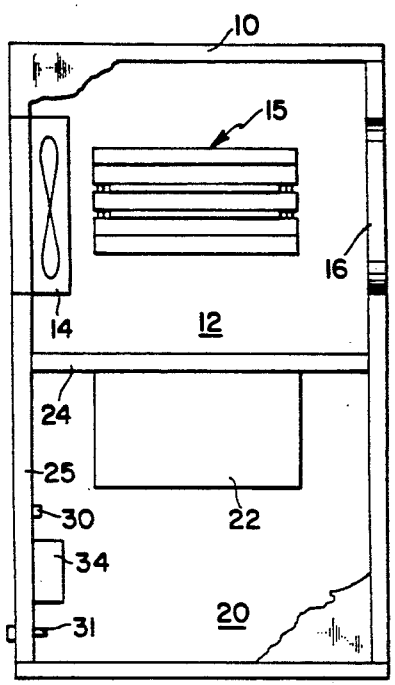
FIG. 1
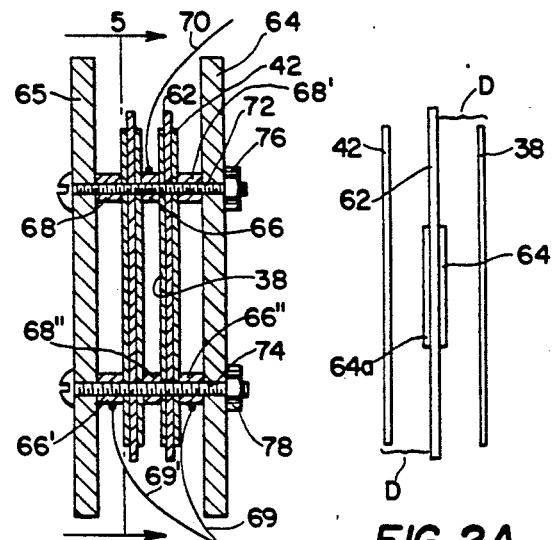
FIG. 2
FIG. 2A
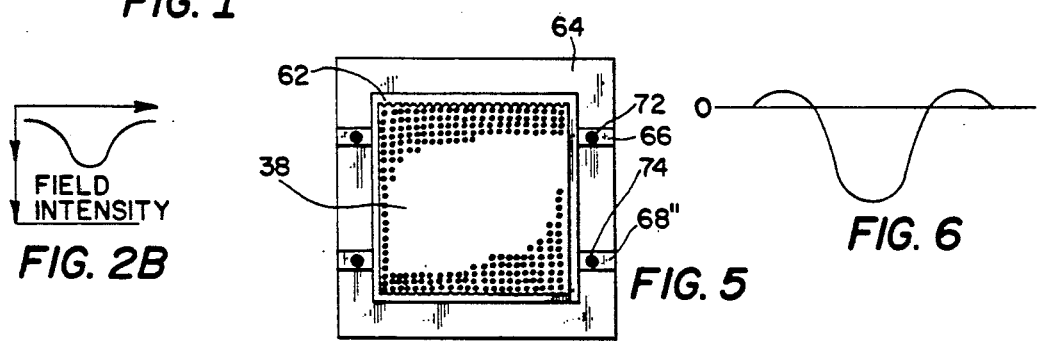
FIG. 2B
FIG. 5
FIG. 6
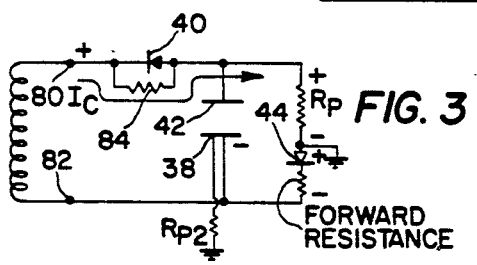
FIG. 3
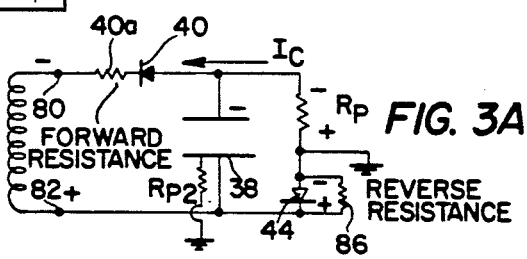
FIG. 3A
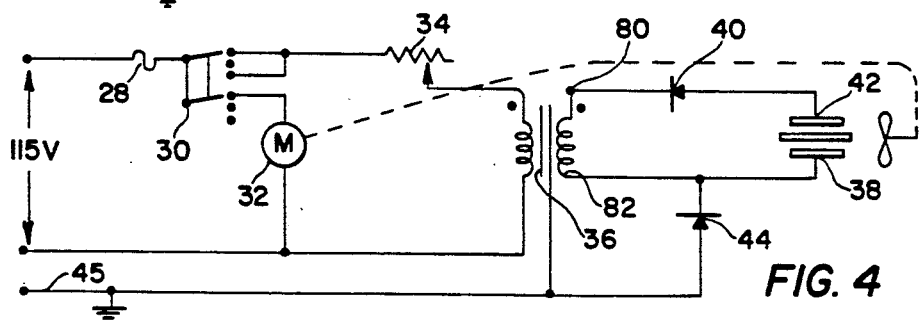
FIG. 4

OZONE GENERATOR

BACKGROUND OF THE INVENTION

This invention relates generally to an apparatus for treating air within a predetermined area and more particularly, to a generator which has a series of parallel plates capable of generating an electric field and ozone within that field. Ozone generators for supplying ozone to a localized region are generally known. Such apparatus typically comprises a housing in which there is located one or more ozone generating units which, when energized, produce ozone gas which may be directed into the room with a fan. Ozone generators have in the past included a pair of electrodes separated by a dielectric member which, when supplied with a high voltage AC source, will cause an electrical discharge between the electrodes. Apparatus of this nature produces nitrous oxide which may be injurious to health. For example, when one of the ozone plates is positively charged, which is half the time, the nitrogen in the ambient air that is passing over the plate receives a positive charge which combines with the oxygen molecules to form nitrous dioxide, nitrous oxide, and possibly, if water vapor is present, nitric acid.

In addition, since ozone generators draw ambient air over the generating plates, there is a problem of accumulating dust and grease on the plates. It is necessary, therefore, to clean the electrodes which is important in a device which tracks particle impurities in the air because periodically, all the particle impurities attracted to the electrodes must be removed. Generally, to clean the generators has involved taking the ozone device apart which is a delicate operation and difficult for someone even skilled.

Accordingly, it is an object of the present invention to provide an improvement in apparatus for treating air in a localized environment.

It is a further object of the invention to provide a mode for operating a generator so that it may be self cleaning.

And yet a further object of the invention is to provide an improved, safe and durable ozone generator which will not produce harmful nitrous oxide in similar products.

SUMMARY OF THE INVENTION

Briefly, the foregoing and other objects in the invention are achieved by an ozone generator comprising at least a pair of electrostatic plates separated by an insulating sheet, which plates receive only negative and less positive charges from each half cycle of the applied alternating current. In the operationally mode, air flows over the electrostatic plates but the fan directing the air over the plates or sucking the air over the plates as the case might be, may be turned off for finite periods to burn off the impurities of other contaminates that might collect thereon.

The ozone generator, therefore, has an air treatment element having at least a pair of plate-like grids with insulation spacing the grids and a power supply means that supplies power across two terminals. One terminal is connected to one grid and also to ground through a blocking diode while the other terminal is connected to the other grid through a blocking diode. Fan means are provided to direct air past the grids and the arrangement is such that both grids maintain negative charges thereon.

DETAILED DESCRIPTION OF THE DRAWINGS

FIG. 1 is a top plan view illustrative of a suitable configuration in a somewhat of diagrammatic form of the invention;

FIG. 2 is a vertical elevational view partly in section illustrating the electrostatic plates sandwiched into an assembly;

FIG. 2A is a detached diagrammatic view of one of the electrostatic plates and the insulating plate;

FIG. 2B is an electrical diagram showing the change in field intensity as the distance D from the electrostatic plate to the insulating plate is varied;

FIGS. 3 and 3A are electrical diagrams showing the equivalent operating circuits;

FIG. 4 is a complete electrical schematic diagram of the air purifying apparatus in accordance with the invention.

FIG. 5 is a sectional view taken on line 5—5 of FIG. 2; and

FIG. 6 is a diagram of the waveform on each plate.

DETAILED DESCRIPTION OF THE PREFERRED EMBODIMENT

Referring now to the drawings, 10 designates a rectangular box or housing which will have a suitable bottom wall and top wall and which is essentially divided into two compartments, there being a compartment 12 for the generation of ozone which will have a suitable fan or blower 14 mounted on a wall member. The fan draws air in through some suitable filter means, not shown, and directs it across the ozone generating unit, generally designated 15 so as to discharge treated air through an opening 16. A second compartment 20 includes a high voltage step-up transformer 22 that is mounted on an internal wall 24 which separates the compartments 12 and 20. For the convenience of the user, the wall 25 of the housing may contain a double pale double throw control rheostat 34, on-off control switch 30 and indicator lights such as 31.

It should be pointed out that the location of the high voltage transformer 22 and the ozone generating unit in a separate compartment serves a very important purpose; namely, in maintaining isolation of the ozone generating unit from any other element that could conceivably contaminate the compartment by either overheating and to maintain the ozone generating units entirely separate from the remaining part of the apparatus.

Referring first to FIG. 4, the AC input line and ground have one side connected through a suitable fuse 28 to a two-pole, three position switch 30, which switch is illustrated as having a center "off" position and is indicated as having an "up" operating position as illustrated which connects the source voltage to one side of a motor 32 and through a variable resistor 34 to the primary of a transformer 36. The transformer may be a 5,000 volt, 10 ma. transformer, one side of whose secondary at 82 is connected to one of the metal plates at 38 while the other side 80 of the secondary is connected through a diode 40 to the other plate as at 42. As seen in the schematic, a diode 44 is connected from the point 38 of the electrostatic plate to ground, ground being provided by the three conductor power cord as indicated at 45.

To understand the operation of the circuit, reference is made to FIGS. 3, 3A and 6. Assume that point 80 on the secondary of transformer is beginning the positive half cycle. Conventional current $I_c$ will flow through the reverse resistance 84 of diode 40, through the plasma resistance $R_p$, then through diode 44 to point 82 of the transformer secondary to complete the circuit. Plate 42 is less positive due to a voltage divider effect of 84 and $R_p$ and a negative charge will be on plate 38 with respect to ground as point 82 is negative. When point 82 begins to go positive, conventional current $I_c$ will flow through reverse leakage resistance 86, through the plasma resistance $R_p$, thence through diode 40 represented by its forward resistance 40a to point 80. The polarity indicated across $R_p$ with respect to ground, results in the charge on plate 42 being negative with respect to ground while the plate 38 is less positive due to the parallel resistances $R_{p2}$ and 86.

The diode 44 is essentially a high voltage diode which has a forward resistance of 3-5 megohms and a reverse internal resistance of from 25-40 megohms. Diode 40 may be similar to a IN4007A silicon rectifier. The rheostat 34 may be a 1,000 ohm 25 watt wire wound unit that is merely in series with the primary of the transformer 36 to control the power output of the circuit.

The generating plates are illustrated in FIG. 2 and consist essentially of a perforated plate such as 60 that is associated with a insulating plate 62 which is preferably an insulating mica sheet suitably laminated so as to have an insulating factor of at least 25 kilovolts per square inch. The perforated plates that provide a multiplicity of sharp edges may be of a suitable metal material such as brass, copper or aluminum and are preferably approximately 0.025 inch thick while the substrate 62 will be on the order of 0.040 inch thick. It has been found that it is advisable to maintain proper spacing D between the substrate and the electrostatic plate 38 or 42. To this end, it has been found advantageous to use a polycellular cushion material such as 64, 64a having a thickness of approximately 0.004 inch that would be secured to the insulating plate 62. The ideal distance between the plate 38 or 42 and the insulating substrate plate 62 is between 0.002"-0.004". It has also been found that this distance is critical and that the field intensity of the plasma discharge will vary until the proper distance is found. To this end the electrostatic plate 42 and plate 38 for example, are compressed toward the substrate until the field intensity rises as seen in FIG. 2B.

In FIG. 2, there is illustrated a suitable manner of constructing the physical arrangement by making a "sandwich" between a pair of insulating brackets 64, 65 that form a support casing. There is then provided conductors 66, 66' and 66" and insulating portions 68, 68' and 68". In essence, by connecting conductors such as 69, 69, to the metallic portions of 66', 66" and a conductor 70 to the conductive metallic portion 66, connections will be made to two sets of spaced, electrostatic plates. In addition, by providing a threaded bolt such as 72, 74 that will threadingly interconnect with the metallic portions and will have a clearance bore in the insulating portions, adjustment of the take-up nuts 76, 78 will change the distance between the electrostatic plates and the insulating substrate such as 62. It has been noted that as the distance varies and as the field intensity increases, there is a change in an audio tone that is essentially a buzz, which can readily be detected by a trained operator so that tuning is rather easily accomplished by simple and inexpensive means.

As noted before, the unit has the advantage of a self-cleaning mode and this is accomplished by a special switch 30 which is a double pole, triple throw type but which in essence, has a position where the electrostatic plates are energized and the fan is not energized. In this position, it puts the apparatus into a self-cleaning mode where the electrostatic plates will clean themselves much like a self-cleaning oven. Usually within thirty minutes to one hour, the plates will have cleaned themselves and the device will then operate as though it were like new. Apparently without the fan circulating the air across the electrostatic plates, the additional contaminates are not brought into the ozone generating area fouling the plates and the grease and other contaminates "burn" off. Ozone is of course continuously generated and it is believed that enough ozone is generated to oxidize grease and other contaminates attached to the plates. It will be understood of course that the switch, while it is described in a particular fashion and in perhaps the most simplistic, may take the form of a separate switch that could turn off the fan or indeed, a timer might be built in series with the motor to turn the motor off for periods of one hour every pre-set time sequence.

We claim:

1. In an ozone generating device having an air treatment element, a source of e.m.f. energizing said element and an electric fan to direct air over the said element, the improvement comprising providing a source of voltage for the element and the fan, at least a double throw switch means connecting the source to either the element alone or to the element and fan whereby when the fan is inoperative and the element is energized the element surfaces will be cleaned of deposited airborne impurities collected on the element.

2. A device as in claim 1 wherein a common source of voltage is provided for the element and the fan.

3. The method of cleaning electrostatic plates in an ozone generator having a voltage connected to spaced plates to create electrical discharge and fan means feeding air past said plates comprising the steps of applying a high voltage to the electrostatic plates and disconnecting the circulating fan for a finite period of time.

4. Apparatus for generating ozone comprising a housing having two compartments, power supply elements located in one compartment, ozone plates located in the other compartment, fan means supplying outside air across the plates, said power supply comprising a high voltage transformer having a secondary winding one end of which is connected to one plate and to the cathode of a first diode, the anode of the first diode being connected to ground, the other end of said secondary connected to the cathode of a second diode whose anode is connected to the said other plate.

5. An ozone generator comprising an air treatment element having a least a pair of electrostatic plates, insulation spacing said plates, a power supply means supplying high voltage across two terminals, one terminal connected to a first plate and to ground through a first blocking diode, the other terminal connected to the second plate through a second blocking diode, fan means to direct air past said plates, whereby the said first plate has a negative charge thereon and the said second plate has a small positive charge relative to said first plate resulting from the voltage divider formed by the reverse resistance of the second diode and the plasma to ground resistance.

6. An ozone generator as in claim 5 wherein the plates and insulation are supported in a casing having outer insulation end brackets, bolts passing from the end brackets through the electrostatic plates, spacer means between the end brackets and the electrostatic plates, compressible spacer means between each plate and the separating insulation whereby the spacing between the plates may be varied to achieve a proper plasma discharge by tightening the said bolts.

7. An ozone generator as in claim 5 where the electrostatic plates ar perforated metal plates.

* * * * *